US006451599B1

(12) United States Patent
Bini et al.

(10) Patent No.: US 6,451,599 B1
(45) Date of Patent: Sep. 17, 2002

(54) MONOCLONAL ANTIBODIES REACTIVE WITH FIBRIN (OGEN) DEGRADATION PRODUCTS GENERATED BY MATRIX METALLOPROTEINASES

(75) Inventors: Alessandra Bini, Astoria, NY (US); Bohdan J. Kudryk, Hillside, NJ (US)

(73) Assignee: New York Blood Center, New York, NY (US)

( * ) Notice: Subject to any disclaimer, the term of this patent is extended or adjusted under 35 U.S.C. 154(b) by 0 days.

(21) Appl. No.: 09/548,895

(22) Filed: Apr. 13, 2000

Related U.S. Application Data

(60) Provisional application No. 60/129,789, filed on Apr. 16, 1999.

(51) Int. Cl.$^7$ .......................... C07K 16/36; C12N 5/20; G01N 33/53; G01N 33/543; G01N 33/558
(52) U.S. Cl. .......................... 435/337; 435/7.1; 435/7.24; 435/7.92; 435/13; 435/69.1; 435/70.21; 436/514; 436/516; 436/518; 436/524; 436/528; 436/529; 436/530; 436/531; 436/534; 436/536; 436/538; 436/548; 436/172; 530/387.3; 530/388.25; 530/391.1; 530/391.3
(58) Field of Search .............................. 435/7.1, 7.24, 435/7.8, 7.92, 7.93, 7.94, 7.95, 13, 7.4, 23, 70.21, 331, 337, 975, 69.1, 452; 436/516, 518, 524, 528, 529, 530, 534, 538, 548, 531, 69, 514, 536, 172; 530/387.3, 387.9, 388.25, 389.3, 391.1, 391.3, 391.7; 424/9.1, 9.34, 133.1, 139.1, 145.1

(56) References Cited

U.S. PATENT DOCUMENTS 5,387,504 A   2/1995 Mumford et al.
5,830,468 A * 11/1998 Bini .......................... 424/94.67
6,043,087 A *  3/2000 Bini et al. .................. 435/337

FOREIGN PATENT DOCUMENTS

WO          99/05361     *  2/1999

OTHER PUBLICATIONS

Bini et al., 1996. Degradation of cross–linked fibrin by matrix metalloproteinase 3 (stromelysin 1): hydrolysis of the gamma Gly 404–Ala 405 peptide bond. Biochemistry 35: 13056–13063.*

Kudryk et al., Oct. 1998. An antibody with ability to discriminate between fragment D/D–dimer formed by matrix metalloproteinases or plasmin. Blood Coagul. Fibrinol. 9: 692.*

Kudryk et al., 1989. "Monoclonal antibodies as probes for fibrin(ogen) proteolysis," in Monoclonal Antibodies in Immunoscintigraphy (J–F. Chatal, ed.) CRC Press, Boca Raton, FLA, pp. 365–398.*

Joan H. Sobel, et al., "Antipeptide Monoclonal Antibodies to Defined Fibrinogen Aα Chain Regions: Anti– Aα487–498, a Structural Probe for Fibrinogenolysis", *Blood*, vol. 91, No. 5 (Mar. 1, 1998): pp 1590–1598.

S. Raut, et al., "Evaluation of the Fibrin Binding Profile of two Anti–Fibrin Monoclonal Antibodies", *Thrombosis and Haemostasis*, 76 (1) 56–64, 1996.

Ken'ichi Obata et al., "A one–step sandwich enzyme immunoassay for human matrix metalloproteinase 3 (stromelysin–1) using monoclonal antibodies", *Clinica Chimica Acta*, 211(1992) 59–72.

Alessandra Bini, et al., "Noncollagenous Bone Matrix Proteins, Calcification, and Thrombosis in Carotid Artery Atherosclerosis", *Arterioscler Thromb Vasc Biol.*, 1999, 19: 1852–61.

Alessandra Bini, et al., "Characterization of Stromelysin 1 (MMP–3), Matrilysin (MMP–7), and Membrane Type 1 Matrix Metalloproteinase (MT1–MMP) Derived Fibrin(ogin) Fragments D–Dimer and D–like Monomer: NH$_2$–Terminal Sequences of Late–Stage Digest Fragments", Laboratory of Blood Coagulation Biochemistry, Lindsley F. Kimball Research Institute, New York Blood Center, New York, vol. 38, No. 42, pp. 13928–13936.

Konttinen et al., "Analysis of 16 different matrix metalloproteinases (MMP–1 to MMP–20) in the synovial membrane: different profiles in trauma and rheumatoid arthritis", *Ann. Rheum. Dis.* Nov. 1999 58 11: 691–697.

Bos, et al., "An enzyme immunoassay for polymophonuclear leucocyte–mediated fibrinogenolysis", European Journal of Clinical Investigation (1997) 27, 148–156.

* cited by examiner

*Primary Examiner*—Christopher L. Chin
*Assistant Examiner*—James L. Grun
(74) *Attorney, Agent, or Firm*—Hoffmann & Baron, LLP

(57) ABSTRACT

The invention provides monoclonal antibodies which are reactive with fibrin(ogen) degradation products (FDPS) generated by matrix metalloproteinases (MMPs), such as MMP-3, MMP-7, and membrane-type 1, MT1-MMP proteolysis of fibrinogen and cross-linked fibrin (and not plasmin or other proteases). Monoclonal antibodies of the invention include, but are not limited to, H5, F2, 90/2, 90/5, B4, 13, C6, A6, G6, E6, 197-1 and 197-2. This invention also provides methods of using monoclonal antibodies for detection of FDPs generated by proteolysis of fibrin(ogen) by MMPs, such as MMP-3, MMP-7, and MT1-MMP. In addition, the present invention provides methods for diagnosing rheumatoid arthritis, osteoarthritis, and synovitides, as well as angiogenesis, atherosclerosis, renal diseases, malignancy and inflammation. The present invention also provides methods for diagnosing fibrin formation and degradation in physiological processes such as in wound healing deficiencies and abnormalities, and in development of human placenta and in pregnancy diseases.

25 Claims, 7 Drawing Sheets

MONOCLONAL ANTIBODIES REACTIVE WITH FIBRIN (OGEN) DEGRADATION PRODUCTS GENERATED BY MATRIX METALLOPROTEINASES This application claims the benefit of the filing date of U.S. provisional application Serial No. 60/129,789 filed Apr. 16, 1999, the entire text of which is hereby incorporated by reference.

FIELD OF THE INVENTION

This invention relates to monoclonal antibodies which are reactive with fibrin(ogen) egradation products (FDPs) generated by proteolysis of fibrinogen and cross-linked fibrin with matrix metalloproteinases (MMPs). More particularly, the invention relates to monoclonal antibodies which are reactive with FDPs generated by proteolysis of human fibrin(ogen) with metalloproteinases, including stromelysin, matrilysin, and membrane-type metalloproteinases, such as MMP-3, MMP-7, and MT1-MMP.

BACKGROUND OF THE INVENTION

Matrix metalloproteinases (MMPs) have the capacity to degrade a number of proteins and proteoglycans that constitute the extracellular matrix of connective tissue. These enzymes participate in the remodeling of tissues in physiological processes such as morphogenesis, embryonic development and angiogenesis, and in the pathophysiology of wound healing, inflammation, tumor invasion, stroke, myocardial infarction, atherosclerosis, arthritis and angiogenesis. The presence of fibrin(ogen)-related antigen (FRA) in vascular and extravascular space has-been described in all of these disease states.

The matrix metalloproteinases ("MMPs" or "matrixins") are a class of enzymes that are expressed within the connective tissues of vertebrates. The MMPs occur natively in such tissues and play critical roles in the continuous processes associated with the laying down and remodeling of the extracellular matrix (ECM), hence their name: "matrix" metalloproteinases. The MMPs can be characterized as "intrinsic" or "endogenous" enzymes insofar as their proper function is within the tissues of the organism in which they are natively expressed. As such, the MMPs are distinguished functionally and evolutionarily from the metalloproteinases found in snake venom and the like, which function outside the organism in which they are expressed, and may therefore be designated "exogenous" enzymes.

MMPs are known to proteolytically cleave and degrade a number of proteins and proteoglycans that are associated with the extracellular matrix (ECM) of connective tissue. They have been shown to break down a number of proteins including collagen (Types I–IV, VII and X), laminin, fibronectin, elastin and proteoglycans. MMPs have also been identified in leukocytes. It has been shown that MMP-2 and MMP-9 possess elastase activity, to which some of the complex proteolytic activity, initially observed in granulocytes, could be attributed. In addition, MMP-12 has also been shown to possess elastin activity. MMP-7 has been shown to possess strong proteolytic activity and digests the connective tissue protein, aggrecan, cartilage link protein, fibronectin, and elastin. MMPs participate in the remodeling of tissues in physiological processes such as morphogenesis, embryonic development, wound healing and angiogenesis. MMPs are also key actors in the pathophysiology of tumor invasion, joint injuries and joint diseases (synovitides), such as rheumatoid arthritis and osteoarthritis, as well as in gout, inflammatory bowel disease (IBD), pulmonary fibrosis and in stroke and atherosclerotic lesions.

The expression of MMPs and their inhibitors is under extensive and precise cellular control by a variety of molecular mechanisms. Known regulating factors include hormones, cytokines, proto-oncogenes, steroids, and growth factors. MMPs are blocked by specific inhibitors called "tissue inhibitors of metalloproteinases" (TIMPs) that can block the activity of each member of the family. The main focus of research on ECM has been to limit ECM degradation by MMPs to interrupt or interfere with the progression of disease states. Several groups of investigators are making small molecules that could inhibit proteinases to alter their destructive activity in arthritis, and as antiangiogenic factors to inhibit tumor spread.

Matrix metalloproteinase 3 (MMP-3 or stromelysin-1) belongs to the stromelysin class of matrix metalloproteinases. MMP-3 is expressed in mature macrophages, but also in endothelial cells, smooth muscle cells and fibroblasts. More recently, MMP-3 has been shown to be expressed in macrophage-derived foam cells from experimental atheroma. The inactive zymogen, proMMP-3, is activated by neutrophil elastase, plasma kallikrein, plasmin, chymotrypsin, trypsin, cathepsin G, and mast cell tryptase, as well as by mercurial compounds, such as 4-aminophenylmercuric acetate (APMA). Elevated levels of MMP-3 have been found in the joints of patients suffering from osteoarthritis and rheumatoid arthritis. In atherosclerotic plaques there is a large amount of fibrin(ogen)-related antigen (FRA) consisting of different molecular forms. Recent studies have shown the presence of matrix metalloproteinases 3 in atherosclerotic plaques. The known substrates of MMP-3 include proteoglycans, collagen type IV, fibronectin, and laminin.

Membrane-type 1 matrix metalloproteinase (MT1-MMP) belongs to the membrane-type matrix metalloproteinases class of MMP. The membrane-type matrix metalloproteinases are a subclass of the matrix metalloprtoteinase family which uniquely possess a C-terminal transmembrane domain and are initiators of an activation cascade for progelatinase A. Recent studies have shown that they can also efficiently directly degrade a number of matrix macromolecules. Specifically, the expression of MT1-MMP on the cell surface may lead to both progelatinase A activation and extracellular matrix degration. MT1-MMP is expressed in various tissues. MT1-MMP MRNA expression is predominantly expressed in lungs, kidneys, and placenta where extracellular matrix remodeling is relatively active, and lowest in the brain. MT1-MMP is expressed at a very high level in ossifying tissues during embryogenesis where gelatinase A is co-expressed. MT1-MMP expression is elevated in various tumor tissues including lung, gastric, colon, and breast cancers, in which activated gelatinase A is expressed. MT1-MMP also exhibits broad-spectrum proteolytic capacities comparable to many matrix metalloproteinases.

Bini et al, *Biochemistry* 35 (40): 13056–13063, 1996 showed that both fibrin(ogen) (Fg) and Factor XlIIa cross-linked fibrin (XL-Fb) can be substrates for MMPs with some differences among the various classes. MMP-1 (or Collagenase) seems to have little effect on both Fg and XL-Fb. MMP-2 (or Gelatinase A), degrades fibrin(ogen) rapidly and extensively. However, Fg degraded with MMP-2 still retain the ability to form a fibrin clot. On the contrary, Fg degraded with MMP-3 (or Stromelysin-1) was unclottable, as was Fg previously degraded with plasmin. One of the three MMPs, namely MMP-3, was the only physiological enzyme, in addition to plasmin, capable of solubilizing XL-Fb.

To the present time, no stable, sensitive and precise means has existed for detecting fibrin(ogen) degradation products (FDPs) generated by proteolysis of fibrin(ogen) and fibrin with matrix metalloproteinases (MMPs). There has been no suggestion, however, that FDPs generated by MMPs, such as MMP-3, MMP-7, and MT1-MMP proteolysis of fibrinogen and cross-linked fibrin (and not plasmin or other proteases) could be detected. Nor has there been any indication that the detection of FDPs generated by MMPs could be used for determining information associated with rheumatoid arthritis, osteoarthritis, synovitides, angiogenesis, atherosclerosis, renal diseases, inflammation, and malignancy, as well as information associated with fibrin formation and degradation in physiological processes such as in wound healing deficiencies and abnormalities, and in development of human placenta, placenta development, and pregnancy diseases.

As a result, there exists a need for highly specific, sensitive and reproducible monoclonal antibodies that are reactive with FDPs generated by MMPs proteolysis of fibrinogen and cross-linked fibrin (and not plasmin or other proteases). In addition, means for diagnostic testing of subjects with respect to the amount and distribution of FDPs generated by MMPs are needed. The present invention effectively addresses these and other needs for the first time.

SUMMARY OF THE INVENTION

The present invention provides monospecific antibodies which specifically bind to fibrin(ogen) degradation products generated by matrix metalloproteinases (MMPs). Particularly preferred MMPs are MMP-3, MMP-7 and MT1-MMP.

The invention further provides a method of detecting a fibrin(ogen) degradation product (FDP) generated by a matrix metalloproteinase (MMP) in a sample, the method comprising: contacting the sample with a monospecific antibody which binds with the fibrin(ogen) degradation product (FDP) generated by the matrix metalloproteinase (MMP), and determining whether there is specific binding of the monospecific antibody in the sample.

The invention yet further provides a kit for the detection of a fibrin(ogen) digestion product (FDP) generated by a matrix metalloproteinase (MMP), comprising: a composition comprising a monospecific antibody which binds with the fibrin) degradation product (FDP) generated by the matrix metalloproteinase (MMP); and a component selected from the group consisting of: a suitable buffer, an FDP standard and a component for detection of the monospecific antibody.

Also provided is a method for diagnosing the presence or probability of a condition, disease or disorder associated with the generation of a fibrin(ogen) digestion product (FDPs) by a matrix metalloproteinase (MMP) in a subject, comprising: providing a sample from the subject, contacting the sample with a monospecific antibody which binds with the fibrin(ogen) degradation product (FDP) generated by the matrix metalloproteinase (MMP), assessing or measuring the specific binding of the monospecific antibody with the sample, and thereby determining the presence or probability of a condition, disease or disorder associated with the generation of the fibrin(ogen) digestion product (FDP) by the matrix metalloproteinase (MMP) in the subject.

Also yet further provided is a method for monitoring a condition, disorder or disease associated with the generation of a fibrin(ogen) digestion product (FDP) by a matrix metalloproteinase (MMP) in a subject, comprising: providing a first sample from the subject to be monitored, contacting the first sample with a monospecific antibody which binds with the fibrin(ogen) degradation product (FDP) generated by the matrix metalloproteinase (MMP), assessing or measuring the specific binding of the monospecific antibody with the first sample from the subject, providing a subsequent sample from the subject, contacting the subsequent sample with the monospecific antibody which binds with the fibrin(ogen) degradation product (FDP) generated by the matrix metalloproteinase (MMP), assessing or measuring the specific binding of the monospecific antibody with the subsequent sample from the subject, and thereby monitoring the condition, disorder or disease associated with the generation of a fibrin(ogen) digestion product (FDP) by a matrix metalloproteinase (MMP) in the subject.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings.

FIG. 1 illustrates the detection of β chains with newly developed monoclonal antibodies in preparations of purified fibrin(ogen) degraded with MMP-3, -7, MT1-MMP and in synovial fluids. FIG. 1C, lanes 8 and 9, non-adsorbed fractions (NA) concentrated by trichloroacetic acid precipitation (TCA, 2:1); FIG. 1D, lanes 2, 4, intact samples (SM); FIG. 1G, lane 7, intact sample (SM); lane 8, non-adsorbed fraction; lanes 9–10, eluted fractions (E2, E3) concentrated by TCA precipitation. (Abbreviations: CCF, Clone Culture Fluid; Fg, fibrin(ogen); XL-fb, cross-linked fibrin; XL-Fb/MMP3, /MMP-7, /MT1-MMP, /MT2/MMP, cross-linked fibrin digested with the indicated MMP; XL-Fb/plasmin, cross-linked fibrin digested with plasmin for the indicated time. Specific antibody-bound fibrin(ogen) chains were detected using peroxidase-labeled rabbit antimouse immunoglobutin (RAMHRPO) and the chemiluminescent substrate.)

DETAILED DESCRIPTION OF THE INVENTION

Figure 1A:
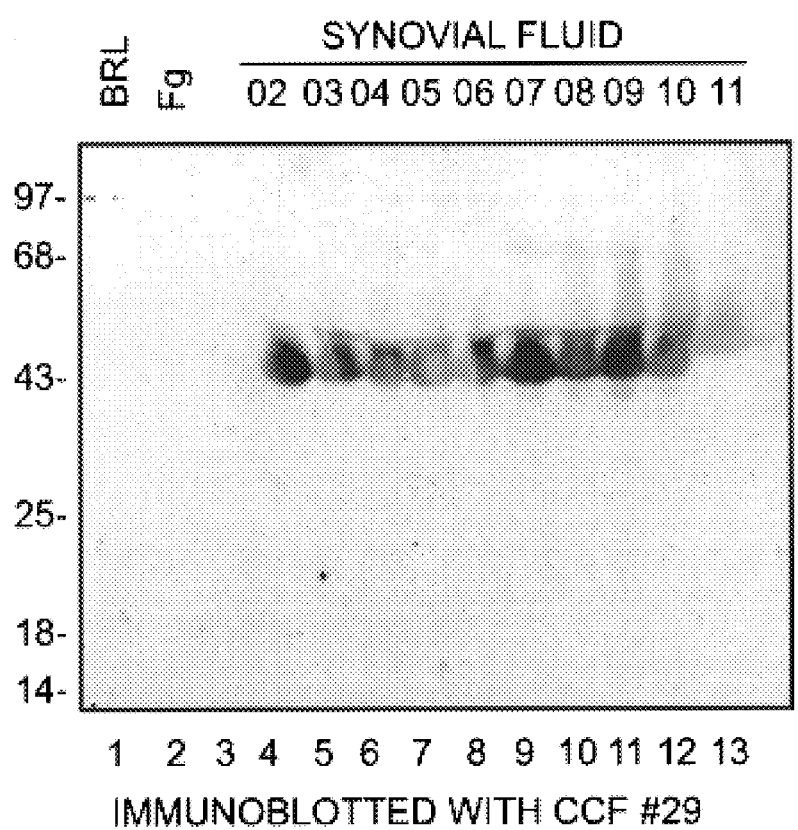
FIGS. 1A and 1B, synovial fluid samples electroblotted with new MoAb/CCF#29 and H5.

As used herein, the term "fibrin(ogen)" refers to fibrin, fibrinogen, and cross-linked fibrin or fragments thereof The term FDPs as used herein refers to Fibrin(ogen) digestion products. FDPs are the products of degradation or digestion by proteases, such as MMPs or plasmin.

The term "MMP" refers to a matrix metalloproteinase. The matrix metalloproteinases ("MMPs" or "matrixins") are a class of enzymes that are expressed within the connective tissues of vertebrates. The MMPs occur natively in such tissues and play critical roles in the continuous processes associated with the laying down and remodeling of the extracellular matrix (ECM).

At least twenty matrix metalloproteinases have been identified to date. These are presently divided into six classes of enzymes: collagenases, gelatinases, stromelysins, matrilysin (formerly PUMP), metalloelastase, and membrane-type metalloproteinases. The membrane-type metalloproteinases class of MMP includes membrane-type 1 MMP (MT1-MMP), membrane-type 2 (MT2-MMP), membrane-type 3 (MT3-MMP), and membrane-type 14 (MMP-14). The collagenase class of MMPs includes interstitial collagenase (MMP-1), neutrophil collagenase (MMP-8), and collagenase-3 (MMP-13). The gelatinase class of MMPs includes gelatinase-A (MMP-2) and gelatinase-B (MMP-9). The stromelysin class of MMPs includes stromelysin-1 (MMP-3), stromelysin-2 (MMP-10), and stromelysin-3 (MMP-11). The matrilysin class of MMPs includes matrilysin (MMP-7). The metalloelastase class of MMPs includes metalloelastase-12 (MMP-12).

ANTIBODIES SPECIFIC FOR FDPs GENERATED BY MMPs

The present invention provides monospecific antibodies that specifically bind fibrin(ogen) degradation products (FDPs) generated proteolysis of fibrin(ogen) and cross-linked fibrin by matrix metalloproteinases (MMPs). More particularly, the invention provides monospecific antibodies which are reactive with or bind to FDPs generated by MMP proteolysis of fibrinogen and cross-linked fibrin, but not plasmin or other proteases.

The present invention provides monoclonal antibodies that are reactive with fibrin(ogen) degradation products generated by MMP, such as for example MMP-3, MMP-7, MT1-MMP. In a particularly preferred embodiment the monoclonal antibodies of the invention include, but are not limited to the following: H5, F2, 90/2, 90/5, B4, 13, C6, A6, G6, E6, 197-1 and 197-2. Additionally these antibodies do not specifically bind FDPs generated by digestion with plasmin or other proteases.

A general method of preparing the antibodies of the invention is described below. Those skilled in the art will recognize that the present invention, including the monoclonal antibodies and hybridoma cell lines described in detail herein, provide a variety of ways to make the monospecific antibodies of the present invention.

A monospecific antibody according to the present invention may be any protein such as an antibody or antigen-binding region thereof, which is reactive with a single epitope or antigenic determinant. Preferably the antibody binds specifically with its cognate antigenic determinant or epitope. The antibodies as disclosed herein may be native, modified, or synthetic, and may include hybrid or chimeric antibodies. The antibody may be polyclonal or monoclonal antibodies. The antibodies of the present invention further include native, modified, synthetic and recombinant antibodies. These include, for example the classical methods of Kohler & Milstein (1976): Derivation of Specific Ab-producing Monoclonal Antibody-producing Tissue Culture and Tumour Cell Lines by Cell Fusion" *Eur. J. Immunol.* 6:511–579; and Kohler & Milstein (1975) *Nature* 245:495.

Alternatively, the antibodies may be prepared by the method of Huse et al., *Science* 246:1275–1281 (1989) or of Coligan et al. (Eds) Current Protocols in Immunology, Wiley Interscience, NY (1999). See also, Harlow and Lane, Using Antibodies, A Laboratory Manual, Cold Spring Harbor Laboratory Press, CSH, NY (1999).

As discussed in the examples below, monospecific antibodies of the invention can be constructed and isolated by immunization, preparation of hybridomas, and identification of antibodies with a reactivity to fibrin(ogen) degradation products generated by MMP.

In the present invention, animals, preferably mice may be used to produce monoclonal antibodies (MoAbs). Since the first published report by the inventors on the preparation of MoAbs to FRA (fibrinogen-related antigens) (Kudryk et al., Molec Immunol 20:1191–1200, 1983 and 21: 89–94, 1984), best results have been obtained with spleen cells from BABLB/c mice immunized with the antigen of choice (for the production of the antibodies herein disclosed, cross-linked fibrin digested with MMP-3 or MMP-7 was used) and fused with a commercial, non-antibody producing myeloma cell line, X63-Ag8.653 from ATCC (American Type Culture Collection, Manassas, Va.).

In further particularly preferred embodiments or the present invention, the hybridomas that can be used to make the monoclonal antibodies of the present invention include, but are not limited to the following: H5, F2, 90/2, 90/5, B4, 13, C6, A6, G6, E6, 197-1 and 197-2.

In another embodiment, the antibodies may be Fab', $F(ab')_2$ or Fv fragments which may be prepared by any of the methods well known to those of skill in the art. Antibody fragments that retain equivalent or comparable epitope-binding specificity as compared to the intact antibody are of particular utility in the methods of the present invention. Such fragments include, but are not limited to Fab, $F(ab')_2$ fragments and Fv fragments. In a preferred embodiment the fragments comprise three or more complementarity-determining regions, CDRs of the intact antibody molecule. More preferably the fragments comprise four CDRs; even more preferably five CDRs and optimally six CDRs.

Fragments may be prepared any of a number of well known methods. For instance, the fragments may be prepared by the methods described by Lamoyi, *Methods in Enzymol.* 121:652-663 (1986) or by Parham *Immunol.* 131:2895–2902 (1983). Specific Fab fragments may be generated using a combinatorial phage display library as described in Clayton, et al. *Biol. Reprod.* 59:1180–1186 (1998), or O'Brien et al. *Proc. Natl. Acad. Sci. USA* 96:640–645 (1999).

ASSAY METHODS FOR FDPs GENERATED BY MMPs

The invention further provides a method of detecting a fibrin(ogen) degradation product (FDP) generated by a matrix metalloproteinase (MMP) in a sample, the method comprising: contacting the sample with a monospecific antibody which binds with the fibrin(ogen) degradation product (FDP) generated by the matrix metalloproteinase (MMP), and determining whether there is specific binding of the monospecific antibody in the sample.

In another aspect, the present invention is directed to the quantitation and localization of FDPs generated by MMPs as a measure of MMP activity or to detect the presence of a particular MMP. The method comprises contacting a sample for testing with an antibody specific for an FDP generated by an MMP. Specific binding of the antibody is indicative of the presence of MMP derived FDPs. These FDPs are thereby detected and may be localized and quantitated by the assay methods described below.

Further, the antibodies of the present invention specifically bind FDPs generated by MMPs, such as for instance, MT1-MMP, MMP-3 and MMP-7. These antibodies may be used to detect the MMP derived FDPs and discriminate them from FDPs derived by plasmin and other proteases which are involved in the normal physiological turnover of fibrin (ogen). For this reason the antibodies of the present invention are particularly useful for detection, diagnosis and monitoring of disorders, diseases and other pathophysiological conditions which lead to breakdown of fibrin(ogen) by MMPs. Alternatively, the antibodies of the present invention may be used for detection, diagnosis and monitoring of sites of injury and wound healing, as for example in joint repair after injury or after surgery.

In yet another embodiment the present invention provides assays for detecting the presence of Fibrin(ogen) digestion products, FDPs produced by MMPs with antibodies. The assay capable of detecting the presence of FDPs produced by MMPs may be any antibody assay. Some suitable assays include standard antibody-based assays, including for example, standard blot assays and ELISA formats. These formats are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well, or by binding the protein to immobilized antibodies.

In a preferred embodiment, known as a sandwich assay, the FDP is captured on a solid support by an immobilized first antibody specific for the protein. The immobilized first antibody is incubated with a sample suspected of containing the FDP. If present, the FDP binds to the first antibody through a first epitope.

A second antibody, also specific for the FDP, binds the immobilized protein through a second epitope. The second antibody may be labelled by methods known in the art. Non-immobilized materials are washed away, and the presence of immobilized label indicates the presence of the protein. This and other immunoassays are described by David, et al. in U.S. Pat. No. 4,376,110 assigned to Hybritech, Inc., La Jolla, Calif.; by Coligan, J. E, et al. (Eds.), Current Protocols in Immunology, Wiley Intersciences, New York, 1999); and by Harlow, E. and Lane, D., Using Antibodies, A Laboratory Manual, Cold Spring Harbor Laboratory Press, Cold Spring Harbor, N.Y. (1999).

Immunoassays may involve one step or two steps. In a one-step assay, the target molecule, if it is present, is immobilized and incubated with a labelled antibody. The labelled antibody binds to the immobilized target molecule. After washing to remove unbound molecules, the sample is assayed for the presence of the label.

In a two-step assay, immobilized target molecule is incubated with an unlabelled first antibody. The target molecule-antibody complex, if present, is then bound to a second, labelled antibody that is specific for the unlabelled antibody. The sample is washed and assayed for the presence of the label, as described above.

The immunometric assays described above include simultaneous sandwich, forward sandwich, and reverse sandwich immunoassays. These terms are well known to those skilled in the art.

In a forward sandwich immunoassay, a sample is first incubated with a solid phase immunoadsorbent containing antibody against the protein. Incubation is continued for a period of time sufficient to allow the protein in the sample to bind to the immobilized antibody in the solid phase. After the first incubation, the solid phase immunoadsorbent is separated from the incubation mixture and washed to remove excess protein and other interfering substances which also may be present in the sample. Solid phase immunoadsorbent-containing protein bound to the immobilized antibodies is subsequently incubated for a second time with soluble labeled antibody cross-reactive with a different domain on the protein. After the second incubation, another wash is performed to remove the unbound labeled antibody from the solid irnmunoadsorbent and to remove non-specifically bound labeled antibody. Labeled antibody bound to the solid phase immunoadsorbent is then detected and the amount of labeled antibody detected serves as a direct measure of the amount of antigen present in the original sample. Alternatively, labeled antibody that is not associated with the immunoadsorbent complex can also be detected, in which case the measure is in inverse proportion to the amount of antigen present in the sample. Forward sandwich assays are described, for example, in U.S. Pat. Nos. 3,867,517; 4,012,294; and 4,376,110.

In a reverse sandwich assay, the sample is initially incubated with labeled antibody. The solid phase immunoadsorbent containing immobilized antibody cross-reactive with a different domain on the protein is added the labeled antibody, and a second incubation is carried out. The initial washing step required by a forward sandwich assay is not required, although a wash is performed after the second incubation. Reverse sandwich assays have been described, for example, in U.S. Pat. Nos. 4,098,876 and 4,376,110.

In a simultaneous sandwich assay, the sample, the immunoadsorbent with immobilized antibody, and labeled soluble antibody specific to a different domain are incubated simultaneously in one incubation step. The simultaneous assay requires only a single incubation and does not require any washing steps. The use of a simultaneous assay is a very useful technique, providing ease of handling, homogeneity, reproducibility, linearity of the assays, and high precision. See U.S. Pat. No. 4,376,110 of David et al.

In each of the above assays, the sample containing antigen, solid phase immunoadsorbent with immobilized antibody and labeled soluble antibody are incubated under conditions and for a period of time sufficient to allow antigen to bind to the immobilized antibodies and to the soluble antibodies. In general, it is desirable to provide incubation conditions sufficient to bind as much antigen as possible, since this maximizes the binding of labeled antibody to the solid phase, thereby increasing the signal. The specific concentrations of labeled and immobilized antibodies, the temperature and time of incubation, as well as other such assay conditions, can be varied, depending upon various factors including the concentration of antigen in the sample, the nature of the sample an the like. Those skilled in the art will be able to determine operative and optimal assay conditions for each determination by employing routine experimentation.

There are many solid phase immunoadsorbents which have been employed and which can be used in the present invention. Well known immunoadsorbents include beads formed from glass, polystyrene, polypropylene, dextran, nylon, and other material; and tubes formed from or coated with such materials, and the like. The immobilized antibodies may be covalently or physically bound to the solid phase immunoadsorbent, by techniques such as covalent bonding via an amide or ester linkage or by absorption.

Antibodies of the present invention may be labeled with any detectable group, such as fluorescent labels, enzyme labels, and radioactive labels to identify fibrin(ogen) degradation products generated by MMP. Detector groups useful according to the invention include, for example, fluorescein as a fluorescent label, horseradish peroxidase as an enzyme label, and Iodine-125 as a radioactive label. Additional fluorescent labels which can be utilized in the invention include, but are not limited to, rhodamine, phycoerythrin and additional compounds emitting fluorescent energy. Additional enzyme labels which can be utilized in this invention include, but are not limited to, glucose oxidase and alkaline phosphatase. Additional radioactive labels which can be utilized in this invention include, but are not limited to, Iodine-131 and Indium-111.

Suitable detectable labels may be selected from among those known in the art, including, but not limited to, radioactive labels, enzymes, specific binding pair components, (such as, for instance biotin and avidin), colloidal dye substances, fluorochromes, reducing substances, latexes, digoxigenin, metals, particulates, dansyl lysine, antibodies, protein A, protein G, protein L, electron dense materials, chromophores, fluorescence resonance energy transfer (FRET) labels, bacterial luminescence resonance energy transfer (BRET) labels and the like. Effectively, any suitable label, whether directly or indirectly detectable, may be employed. One skilled in the art will clearly recognize that these labels set forth above are merely illustrative of the different labels that could be utilized in this invention.

The antibodies of the invention can also be derivatized by conjugation to biotin, and used, upon addition of species of avidins which have been rendered detectable by conjugation to fluorescent labels, enzyme labels, radioactive labels, electron dense labels, etc., in a multiplicity of immunochemical and immunohistological applications.

The monospecific antibodies of the invention may also be attached or bound to substrate materials according to methods known to those skilled in the art. Such materials are generally substantially solid and relatively insoluble, imparting stability to physical and chemical disruption of the antibodies, and permitting the antibodies to be arranged in specific spatial distributions as well as facilitating washing procedures and replacement of the medium in which the antibodies are stored and used. Among substrate materials, materials may be chosen according to the artisan's desired ends, and include materials such as gels, hydrogels, resins, beads, nitrocellulose, nylon filters, microtiter plates, culture flasks, polymeric materials, and the like, without limitation.

The monospecific antibodies of the present invention, whether labeled or unlabeled, can be used in immunological assays to determine the presence of fibrin(ogen) degradation products generated by MMP in tissue samples from human or animal subjects. Biopsy and necropsy samples of subjects, as well as samples from tissue libraries or blood banks, can be evaluated for the presence of fibrin(ogen) degradation products generated by MMP using an antibody of this invention. Moreover, suitable pharmaceutical preparations according to the invention may be employed for in vivo use, such as for the visualization of fibrin(ogen) or fibrin(ogen)-containing substances and structures in a living subject. The immunological assay for detection of FDPs generated by MMPs may be an immunohistochemical assay using the FDP-specific antibodies of the present invention Standard, well known immunohistochemical and cytohistochemical methods are readily available, such as, for example, the methods described in Ciocca et al. "Immunohistochemical Techniques using Monoclonal antibodies" *Meth. Enzymol.* 121:562–579.

Thus, the invention provides a method for binding the fibrin(ogen) degradation products generated by matrix metalloproteinases. Accordingly, fibrin(ogen) degradation products generated by MMP can be detected, assessed or measured by means of monoclonal antibodies of the invention.

In the binding method of the invention, the method includes contacting a sample, in which the presence or absence of degradation of fibrin(ogen) by MMP is to be determined, with a composition comprising a monoclonal antibody. The method then involves measuring an amount of specific association or binding between the fibrin(ogen) degradation products generated by MMP and the monoclonal antibody. In this method, specific binding of the antibody in the sample indicates the presence of fibrin(ogen) degradation products generated by MMP in the system. The sample can be either in vivo or in vitro, and the method of the invention can be performed in vivo, in vitro, or a combination thereof, such as in ex-vivo therapy here the sample is obtained from a subject and is replaced after treatment outside of the subject.

The compositions and methods of the present invention applied to the detection or quantitation of FDPs generated by MMPs may be particularly useful for the diagnosis of and the monitoring of treatment of a wide variety of diseases and disorders. These include, but are not limited to, for example, rheumatoid arthritis, osteoarthritis, and other synovitides, as well as atherosclerosis, renal diseases, and malignancies such as invasive carcinomas.

The compositions and methods of the present invention are also useful in diagnostic methods for determining information associated with fibrin formation and degradation in physiological processes such as in wound healing (such as in repair of joint injuries) and in development of human placenta and placenta development diseases. For example, the antibodies of the present invention may be used to monitor the progress of wound healing, or the efficacy of treatment for conditions, disorders or diseases that involve the degradation of fibrin(ogen) by MMPs to form FDPs.

In another example, the monospecific antibodies of the present invention may be used to detect, diagnose or monitor the progress of treatment of physiological or pathophysiological conditions such as normal or abnormal placental development which may be characterized by different levels of FDPs generated by MMPs.

In a preferred embodiment, the detection method employs a monospecific antibody which has been detectably labeled with a marker moiety. In other embodiments, the method may employ a monospecific antibody of the invention which has been bound to a substrate material. In the method, the composition may also include other reagents such as other antibodies which differentially detect other fibrin(ogen) subunits or subtypes.

The fibrin(ogen) binding method of the invention includes methods known in the art which employ antibodies to specifically bind target substances. Preferred methods include immunochemical methods, such as enzyme-linked immunosorbent assay (ELISA) methods, immunonephelometry methods, agglutination methods, precipitation methods, immunodiffusion methods, immunoelectrophoresis methods, immunofluorescence methods, scintillation proximity assays and radioimmunoassay methods.

The invention further provides monospecific antibodies which are attached, bound or conjugated (through methods known in the art) to other moieties such as detectable label moieties and substantially solid substrate materials. Such molecules are referred to as immunoconjugates. For example the immunoconjugates of the invention include antibodies which are detectably labeled. Suitable detectable label moieties may be selected from among those known in the art. The immunoconjugates of the invention may be bound to a solid substrate such as for example, a plastic plate well, or to a substantially solid substrate, such as for example a resin or semi-solid substrate. Substantially solid substrate materials may also be chosen according to the artisan's desired ends. U.S. Pat. No. 5,811,265 entitled "Hybrid immunoglobulin-thrombolytic enzyme molecules which specifically bind a thrombus, and methods of their production and use" discloses compositions and methods of particular interest and utility in combination with the present invention and is hereby incorporated by reference. The methods disclosed relate to thrombus binding antibody-enzyme hybrid compositions for targeting thrombolytic activities.

In another embodiment the antibodies of the present invention form part of an inimunoconjugate or fusion protein for antibody targeting of therapeutic agents. The fusion or conjugate component in addition to the FDP specific antibody may be for example, a drug molecule, an enzyme, an imaging agent, an analgesic, a growth factor or a toxin. These molecules may be used in treatment of a subject with a condition, disorder or disease involving FDPs generated by MMPs. The immunoconjugate is chosen to provide an appropriate treatment, as for example a targeted toxin immunoconjugate for a subject having a malignancy producing FDPs by the action of MMPs. Alternatively the immunoconjugate may be an imaging molecule for use in detection, localization and imaging of synovitides, such as for example, rhematoid arthritis or osteoarthritis. The immunoconjugate methods disclosed in U.S. Pat. No. 5,851,527 entitled "Method for antibody targeting of therapeutic agents" are of particular interest and utility in combination with the antibodies of the present invention, the entire specification of which is hereby incorporated by reference.

The invention is also directed to an immunoassay system for detection, diagnosis and monitoring of a condition, disorder or disease involving MMP mediated cleavage of Fibrin(ogen). According to the method of the present invention, a sample form the subject is provided. The sample may be any sample including but not limited to a biological sample. Further, the sample may be tested in vitro or in situ in the subject. The method further comprises contacting the sample with an antibody specific for an FDP generated by an MMP under conditions suitable for specific binding. Specific binding of the antibody is indicative of detection or diagnostic of the condition, disorder or disease.

KITS COMPRISING ANTIBODIES SPECIFIC FOR FDPs GENERATED BY MMPs

The invention further provides detection, diagnostic and monitoring kits, as well as experimental kits which include a monospecific antibody that reacts with fibrin(ogen) degradation products generated by MMP. In these kits, the antibodies may be provided with means for binding to detectable marker moieties or substrate surfaces. Alternatively, the kits may include the antibodies already bound to marker moieties or substrates. The kits may further include positive and/or negative control reagents as well as other reagents for adapting the use of the antibodies of the invention to particular experimental and/or diagnostic techniques as desired. For example, a sample of FDPs generated by MMPs may serve as a positive control, whereas a sample of FDPs generated by plasmin may serve as a negative control for binding of the antibodies of the present invention.

The kits may be prepared for in vivo or in vitro use, and may be particularly adapted for performance of any of the methods of the invention. Thus for example, the kits may be used to detect, diagnose or monitor a condition, disorder or disease associated with FDPs generated by MMPs in a tissue or biological fluid sample, such as a blood sample or synovial fluid sample in vitro. Alternatively, the kits may be used to detect, diagnose or monitor such a condition, disorder or disease in vivo. For example the antibody of the present invention may be injected directly or indirectly into the synovium of a subject undergoing testing.

Further, the kits may be adapted to any of the detection methods disclosed herein, including but not limited to immunoassays, such as for example, western blots, dot blots, immunoprecipitations, ELISAs and RIAs.

In yet another aspect the invention provides kits comprising monospecific antibodies that specifically bind FDPs generated by MMPs. Preferably, the monospecific antibody is a monoclonal antibody or a chimeric antibody. In another embodiment the chimeric antibody may be a humanized antibody. The kits of the present invention may further comprise a suitable buffer for carrying out binding assays.

Alternatively, the kits may comprise the antibody and an FDP standard for comparison with the sample. Suitable standards would include, for example, known or measured amounts of an FDP generated by an MMP. Alternatively, the standard may comprise a known or measured amount of an antigenic compound or epitope recognized by the comprising monospecific antibodies that specifically bind FDPs generated by MMPs.

In another alternative the kits may contain a component for detection of the monospecific antibody. The component for detection of the monospecific antibody may be for example, a second antibody that binds the monospecific antibody that specifically bind FDPs generated by MMPs. Alternatively, the component for detection of the monospecific antibody may be for example, one component of a binding pair, such as avidin and biotin.

In a particularly preferred embodiment the kit of the present invention comprises a monospecific antibody that specifically binds an FDP generated by an MMP labeled with a detectable moiety. The detectable moiety may be for example, a radioactive label, an enzyme, a specific binding pair components, (such as, for instance, biotin and avidin), a colloidal dye substance, a fluorochrome, a reducing substance, a latex, digoxigenin, a metal, a particulate, dansyl lysine, an antibody, protein A, protein G, protein L, an electron dense material, a chromophore, a fluorescence resonance energy transfer (FRET) label, a bacterial luminescence resonance energy transfer (BRET) label and the like. Effectively, any suitable label, whether directly or indirectly detectable, may be employed.

In the kits of the present invention, the monospecific antibody that specifically binds an FDP generated by an MMP may be attached to a solid substrate, such as a plastic plate well, a resin or a bead.

METHODS FOR DETECTION, DIAGNOSIS AND MONITORING

The invention further includes a method for determining or diagnosing the existence of or probability of any condition, disorder or disease associated with FDPs produced by MMPs. Such conditions, disorders and diseases include for example, rheumatoid arthritis, osteoarthritis, and other synovitides, as well as angiogenesis, atherosclerosis, renal diseases, and malignancy. The present invention also provides diagnostic methods for determining information associated with fibrin formation and degradation in physiological processes such as in wound healing and in development of human placenta and placenta development diseases. These methods may be performed in vitro or in vivo. Preferably these methods are immunochemical or cytohistochemical methods as described above.

The antibodies of the present invention are also useful in imaging of FDPs generated by MMPs in samples in vivo or in vitro. The antibodies may be detectably labelled such that the presence and distribution of FDPs from MMP digestion may be detected and scanned or an image formed by any of the well known medical imaging techniques. These include but are not limited to autoradiography, as in X-ray imaging and nuclear magnetic resonance (NMR) imaging etc.

In the methods of the present invention for detection, diagnosis or monitoring, the sample is contacted with an antibody that specifically binds FDPs generated by MMPs under suitable conditions for specific binding to occur. Any specific binding is then determined by any one of the above described methods for detection of the antibody:FDP complex. Thereby a condition, disorder or disease involving production of FDPs by MMPs are detected.

The level of specific binding may be compared with a reference sample from a healthy subject or a subject not suffering form the disease or condition suspected or under investigation. Such reference standards may be obtained by screening a representative number of control subjects not suffering from the disease or disorder, or not exhibiting the condition. The specific binding of the antibody of the present invention with the sample may be compared with the specific binding with the standard sample or control(s) or control population and the diagnosis thereby determined by a person of ordinary skill. The specific binding in a sample from a normal subject may be zero or may fall within a particular range. From such determinations a suitable sample from a normal subject may be identified.

Alternatively the comparison of the specific binding in samples from a particular subject taken at different times allows condition, disorder or disease to be monitored. In one embodiment, the progress of the treatment of a condition, disorder or disease may be monitored to assess its efficacy and progress.

In the methods for detection, diagnosis and monitoring of conditions, disorders or diseases associated with FDPs produced by MMPs, a sample is provided for testing. The sample may be any sample, but biological samples are preferred. A biological sample may be a tissue sample or a biological fluid, such as for example blood, plasma, lymph, synovial fliud cerebrospinal fluids, secretions, and cellular and tissue extracts and fluids. The sample may be provided from the subject or may be tested in situ in the subject, as for instance in testing of synovial fluid samples in vitro or ini vivo in the synovium.

In a preferred embodiment the detection, diagnostic and monitoring methods of the present invention are immunoassay methods. Such immuno-assays include for example, but not limited to RIAs, ELISAs, and immunoblot analysis using the MoAbs of the present invention(especially H5, F2, 90/2, 90/5). These methods are useful in determining in vivo proteolysis of fibrin(ogen) by MMP-3, 7, MT1-MMP or other MMPs. Since Fg, XL-Fb and early and late plasmin digest of XL-Fb are totally unreactive with antibodies B4, I3, C6, 197/1, 197/2 in addition to H5, F2, 90/2 and 90/5-any reactivity with plasma, other body fluids and tissue fibrin (ogen)-derived deposits would be strongly suggestive of in vivo presence of MMP-3, -7 and MT1-MMP activity on fibrin(ogen).

These antibodies are also especially useful in methods for early detection and diagnosis of inflammatory and non-inflammatory joint disease such as rheumatoid arthritis, osteoarthritis and others in which fibrin deposits are present in the affected joints. In these diseases the fibrin deposits are degraded by a number of proteases including plasmin and MMPs. Moreover, those antibodies may be utilized to evaluate the proteolytic activity of MMPs in angiogenesis and a number of diseases in which circulating or tissue FDPs have been previously detected. These include diseases such as, for example, inflammation, atherosclerosis, renal disease, malignancy and others known to involve fibrin(ogen) degradation by MMP activity.

The antibodies antibodies of the present invention are also useful in detecting, diagnosing and monitoring thrombolytic events, such as for instance, myocardial infarction, pulmonary embolism, stroke and deep vein thrombosis. See for example, U.S. Pat. No. 5,843,690 entitled "Immunoassay and kit for in vitro detection of soluble desAABB fibrin polymers." Furthermore, these antibodies may be utilized to study fibrin formation and degradation in physiological processes such as, for example in wound healing, and also in the development of human placenta and in diseases of placental development.

RECOMBINANT ANTIBODIES

The antibodies of the invention that specifically bind FDPs generated by MMPs include recombinant antibodies. These recombinant antibodies may be, for example, chimeric antibodies. In an alternative embodiment the recombinant antibodies may be, for example, fusion proteins. Recombinant antibodies of the invention may also be prepared by providing DNA that encodes the antibody; amplifying or cloning the DNA in a suitable host; expressing the DNA in a suitable host; and harvesting the antibody and in certain embodiments the antibody may be further purified.

A. Providing DNA

Chemical Synthesis from Nucleotides.

The DNA may be synthesized chemically from the four nucleotides (A, T. G and C) in whole or in part by methods known in the art. Such methods include those described by Caruthers in Science 230:281–285 (1985) and DNA Structure, Part A: Synthesis and Physical Analysis of DNA, Lilley, D. M. J. and Dahlberg, J. E. (Eds.), Methods Enzymol., 211, Academic Press, Inc., New York (1992).

Alternatively, the nucleic acid molecules of the invention may be isolated from the available cDNA libraries and screened with selected probes comprising epitopes recognized by the antibodies of the present invention. See Sambrook, J. et al. (eds), Molecular Cloning, Second Edition, Cold Spring Harbor Laboratory Press, Cold Spring Harbor, N.Y. (1989) and Ausubel, F. M. et al. (eds), Current Protocols in Molecular Biology, John Wiley & Sons, New York (1999).

DNA may also be synthesized by preparing overlapping double-stranded oligonucleotides, filling in any gaps with polymerase I, and ligating the ends together with DNA ligase. The DNA may be cloned in a suitable host cell and expressed in the same cell or isolated and transformed in a host cell more suitable for expression. The DNA and protein may be recovered from the host cell. See, generally, Sambrook, J. et al. (Eds.), Molecular Cloning, Second Edition, Cold Spring Harbor Laboratory Press, Cold Spring Harbor, N.Y. (1989) and Ausubel, F. M. et al. (Eds.), Current Protocols in Molecular Biology, John Wiley & Sons, Inc., New York (1999).

B. Expressing DNA

The DNA encoding the antibody of the invention may be replicated and used to express ecombinant protein following insertion into a wide variety of host cells in a wide variety of cloning and expression vectors. The host may be prokaryotic or eukaryotic. The DNA may be obtained from natural sources and, optionally, modified. The genes may also be synthesized in whole or in part.

Cloning vectors may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as lambda and M13 or fd, and other filamentous single-stranded DNA phages.

Vectors for expressing antibody in bacteria, especially *E. coli*, are also known. Such vectors include the pK233 (or any of the tac family of plasmids), T7, pBluescript II, bacteriophage lambda ZAP, and lambda $P_L$ (Wu, R. (Ed.), Recombinant DNA Methodology II, Methods Enzymol., Academic Press, Inc., New York, (1995)). Examples of vectors that express fuision proteins are PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. [see addition from SKE-1-P] Other expression vector systems are based on beta-galactosidase (pEX); maltose binding protein (pMAL); glutathione S-transferase (pGST or PGEX)—see Smith, D. B. Methods Mol. Cell Biol. 4:220–229 (1993); Smith, D. B. and Johnson, K. S., Gene 67:31–40 (1988); and Peptide Res. 3:167 (1990), and TRX (thioredoxin) fusion protein (TRXFUS)—see LaVallie, R. et al., Bio/Technology 11:187–193 (1993).

Vectors useful for cloning and expression in yeast are available. Suitable examples are $2\mu$m circle plasmid, Ycp50, Yep24, Yrp7, Yip5, and pYAC3 (Ausubel, F. M. et al. (Eds.), Current Protocols in Molecular Biology, John Wiley & Sons, Inc., New York, (1999)).

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e. shuttle vectors, allow for the isolation and identification of protein coding sequences in prokaryotes.

Further eukaryotic expression vectors are known in the art (e.g., P. J. Southern and P.

Berg, J. Mol. Appl. Genet. 1:327–341 (1982); S. Subramani et al, Mol. Cell. Biol. 1:854–864 (1981); R. J. Kaufmann and P. A. Sharp, "Amplification And Expression Of Sequences Cotransfected with A Modular Dihydrofolate Reductase Complementary DNA Gene," J. Mol. Biol. 159:601–621 (1982); R. J. Kaufmann and P. A. Sharp, Mol. Cell. Biol. 159:601–664 (1982); S. I. Scahill et al, "Expression And Characterization of The Product of a Human Immune Interferon DNA Gene In Chinese Hamster Ovary Cells," *Proc. Natl. Acad. Sci. USA* 80:4654–4659 (1983); G. Urlaub and L. A. Chasin, *Proc. Natl. Acad. Sci. USA* 77:4216–4220 (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, the tet system, the major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as SG-936, HB 101, W3110, X1776, X2282, DH1, DH5αF', and MRC1, Pseudomonas, Bacillus, such as *Bacillus subtilis*, and Streptomyces. Suitable eukaryotic cells include yeasts and other fungi, insect, animal cells, such as COS cells and CHO cells, human cells and plant cells in tissue culture.

C. Fusion Proteins

The antibodies of the invention may be expressed in the form of a fusion protein with an appropriate fusion partner. The fusion partner preferably facilitates purification and identification and may subsequently be cleaved from the antibody of the present invention. Increased yields may be achieved when the fusion partner is expressed naturally in the host cell. Some useful fusion partners include beta-galactosidase (Gray, et al., Proc. Natl. Acad. Sci. USA 79:6598 (1982)); trpE (Itakura et al., Science 198:1056 (1977)); protein A (Uhlen et al., Gene 23:369 (1983)); glutathione S-transferase (Smith, D. B., Methods Mol. Cell Biol. 4:220–229 (1993); Smith, D. B. and Johnson, K. S., Gene 67:31–40 (1988); Johnson, Nature 338:585 (1989)); Van Etten et al., Cell 58:669 (1989)); and maltose-binding protein (Guan et al., Gene 67:21–30 (1987); Maina et al., Gene 74:36–373 (1988), in Ausubel, F. M. et al. (Eds.) Current Protocols in Molecular Biology, John Wiley & Sons, Inc., New York (1999)). Alternatively, the fusion protein may comprise a poly-Histidine metal binding domain, such that the protein may be purified by binding to and eluted from an immobilized metal compound, such as a manganese compound.

Such fusion proteins may also be purified by affinity chromatography using reagents that bind to the fusion partner. The reagent may be a specific ligand of the fusion partner or an antibody, preferably a monoclonal antibody. For example, fusion proteins containing beta-galactosidase may be purified by affinity chromatography using an anti-beta-galactosidase antibody column (Ulhnan, Gene. 29:27–31 (1984)). Similarly, fusion proteins containing maltose binding protein may be purified by affinity chromatography using a column containing cross-linked amylose; see Guan, European Patent Application 286,239.

The protein may occur at the amino-terminal or the carboxy-terminal side of the cleavage site. Optionally, the DNA that encodes the fusion protein is engineered so that the fusion protein contains a cleavable site between the protein and the fusion partner. Both chemical and enzymatic cleavable sites are known in the art. Suitable examples of sites that are cleavable enzymatically include sites that are specifically recognized and cleaved by collagenase (Keil et al. FEBS Letters 56:292–296 (1975)); enterokinase Prickett, K. S. et al., Biotechniques 7:580–589 (1989); LaVallie et al., J. Biol. Chem. 268:23311–23317 (1993)); factor Xa (Nagai et al., Methods Enzymol. 153:461–481 (1987)); and thrombin (Eaton et al., Biochemistry 25:505 (1986) and Chang, J. Y. Eur. J. Biochem. 151:217–224 (1985)). Collagenase cleaves between proline and X in the sequence Pro-X-Gly-Pro wherein X is a neutral amino acid. Enterkinase cleaves after lysine in the sequence Asp-Asp-Asp-Asp-Lys. Factor Xa cleaves after arginine in the sequence Ile-Glu or Asp-Gly-Arg. Thrombin cleaves between arginine and glycine in the sequence Arg-Gly-Ser-Pro.

Specific chemical cleavage agents are also known. For examples, cyanogen bromide cleaves at methionine residues in proteins (Gross,E., Methods Enzymol. 11:238–255 (1967), hydroxylamine cleaves at Asn-Gly bonds (Bornstein, G. and Balian, G., J. Biol. Chem. 245:4854–4856 (1970), and by hydrolysis at low pH (Asp-Pro bonds are labile at low pH) Landon, M., Methods Enzymol. 47(E):145–149 (1977).

In another embodiment, the antibodies of the present invention may be incorporated into a multivalent antibody, such as for instance a bispecific antibody. Bispecific antibodies are designed with dual antigenic specificities and prepared by chemically linking two different monoclonal antibodies or by fusing two hybridoma cell lines to produce a hybrid-hybridoma. Bispecific antibodies are being developed as new agents for immunotherapy as described, for example, in Brennan, M. et al., Science 229:81–83 (1985); in Paulus, H., Behring Inst. Mitt. 78:118–132 (1985); in Rammensee, H.G. et al., Eur. J. Immunol. 17:433–436 (1987); in Segal, D. M. et al., Princess Takamatsu Symp. 19:323–331 (1988); in Kranz, D. M. et al., J. Hematother. 4:403–408 (1995); and in Morimoto, K. and Inouye, K. J. Immunol. Methods 224:43–50 (1999). Multivalent antigen binding proteins are disclosed in U.S. Pat. No. 6,027,725 the specification of which is hereby incorporated by reference. These multivalent antibodies including single chain antibodies, and multivalent chains produced from purified monomers.

In yet another embodiment the monospecific antibodies according to the present invention are admixed with a pharmaceutically acceptable substance to form pharmaceutical compositions suitable for clinical administration. Many pharmaceutically acceptable substances are well known to those of skill in the art, including for example, pharmaceutical carriers, solvents, salts, excipients, physiological substances and bulking agents. In a preferred embodiment the antibodies of the present invention which comprise the pharmaceutical composition are chimeric antibodies.

In a particularly preferred embodiment, the chimeric antibodies are humanized antibodies suitable for clinical administration. Humanized antibodies are antibodies wherein the constant regions are derived from human antibodies and one or more light or heavy chain variable region (complementarity-determining region, or CDR) is derived from a non-human source. U.S. Pat. No. 5,939,531 discloses "Recombinant Antibodies specific for growth factor receptor" and U.S. Pat. No. 6,020,153 discloses "Chimeric antibodies." U.S. Pat. No. 6,037,454 is entitled "Humanized anti-CD11A antibodies" and discloses methods for making antibodies suitable for use in combination with the present invention.

EXAMPLES

Example 1

In the present studies on Fibrin(ogen) degradation by MMP-3, MMP-7 and MT1-MMP, it has been shown by amino terminal sequence analysis that the cleavage sites for those enzymes are different from those cleaved by plasmin (Bini et al, Thromb Haemost, submitted). Additionally, the present inventors have been able to distinguish MMP-3, MMP-7 and MT1-MMP from both early and late plasmin degradation products of fibrin(ogen) using specific monoclonal antibodies (Bini et al. FASEB J, in press). These antibodies are used to detect FDPs generated by proteolysis with MMP-3, MMP-7 and MT1-MMP in vivo and have detected the presence of such products in synovial fluid from patients with rheumatoid arthritis, osteoarthritis and other synovitides (inflammatory and non-inflammatory, as well as degenerative diseases of the joints) (Bini et al. FASEB J, in press).

Example 2

Monoclonal antibodies including F2, H5, 90/2, 90/5 were isolated from two fusion experiments using spleen cells of animals sensitized with XL-Fb fully digested with MMP-3 or MMP-7. After immunizing with mixtures of such degradation products, antibodies were identified which were specific for fibrin(ogen) degradation products (FDPs) generated by degradation of XL-Fb with MMP-3 and MMP-7, but not reactive with intact Fg, XL-Fb or early and late FDPs generated by degradation of fibrin(ogen) with plasmin. As shown in FIGS. 1E and 1F, monoclonal antibodies H5 and F2 are specific for XL-Fb degraded with MMP-3, -7 and MT1-MMP (lanes 4–6). However, neither antibody reacted with intact Fg, XL-Fb (lanes 2, 3) and FDPs obtained after degradation of XL-Fb with MT2-MMP (lanes 7, 8) and early and late plasmin digest of XL-Fb (lanes 9, 10).

Figure 1B:
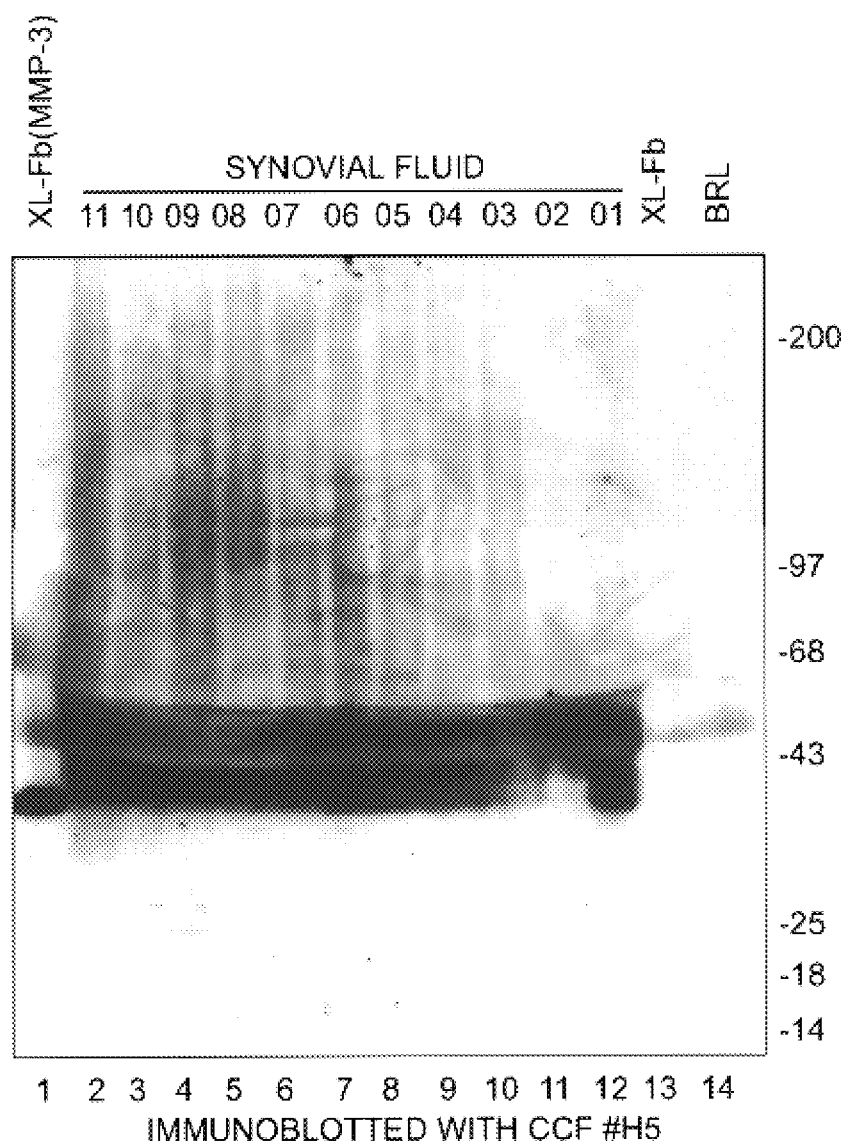
Figure 1C:
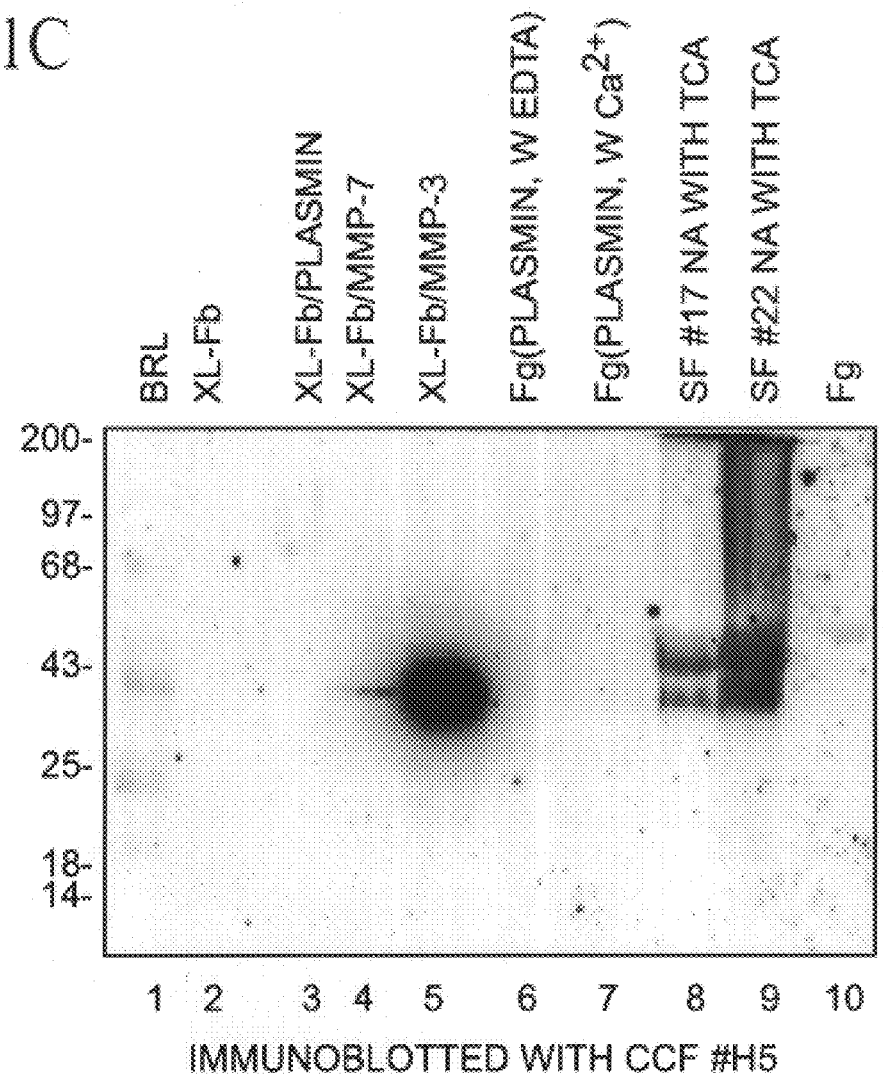
FIGS. 1C, 1D, and 1G, Two synovial fluids from patients with osteoarthritis (#17) and rheumatoid arthritis (#22) were purified by affinity chromatography on a MoAb/2N3H10 column (MoAb to E-domain).
Figure 1D:
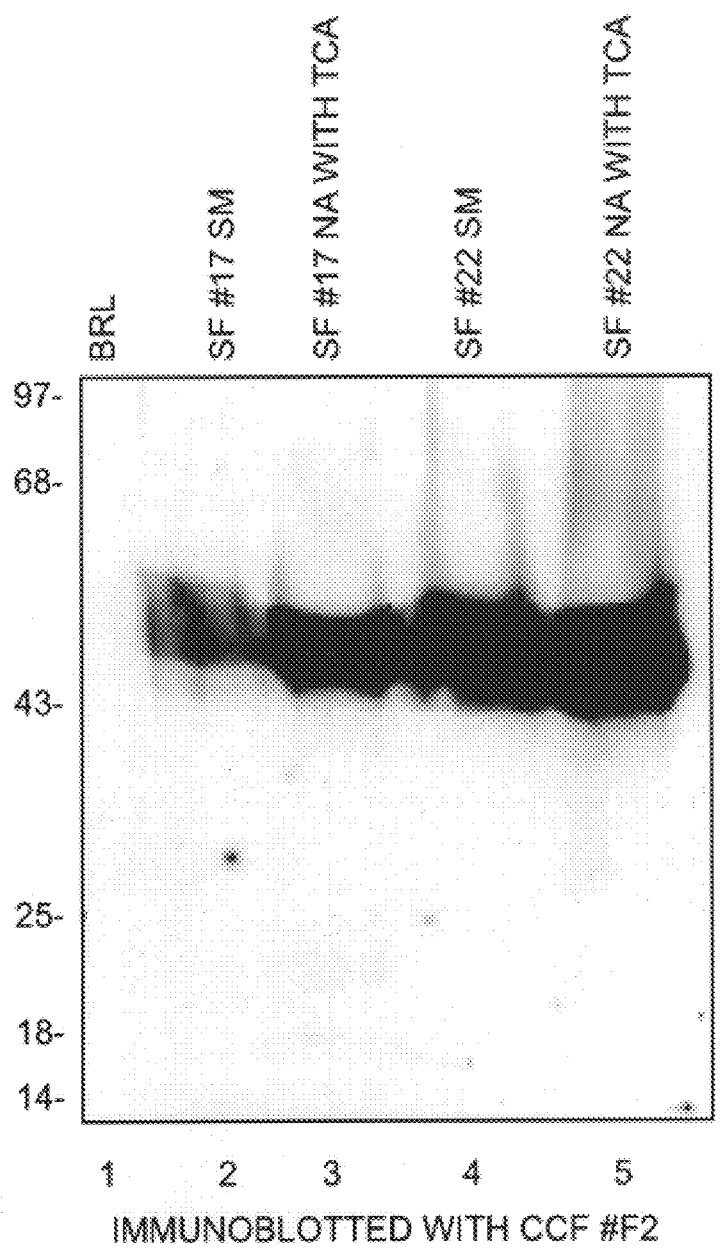
Figure 1E:
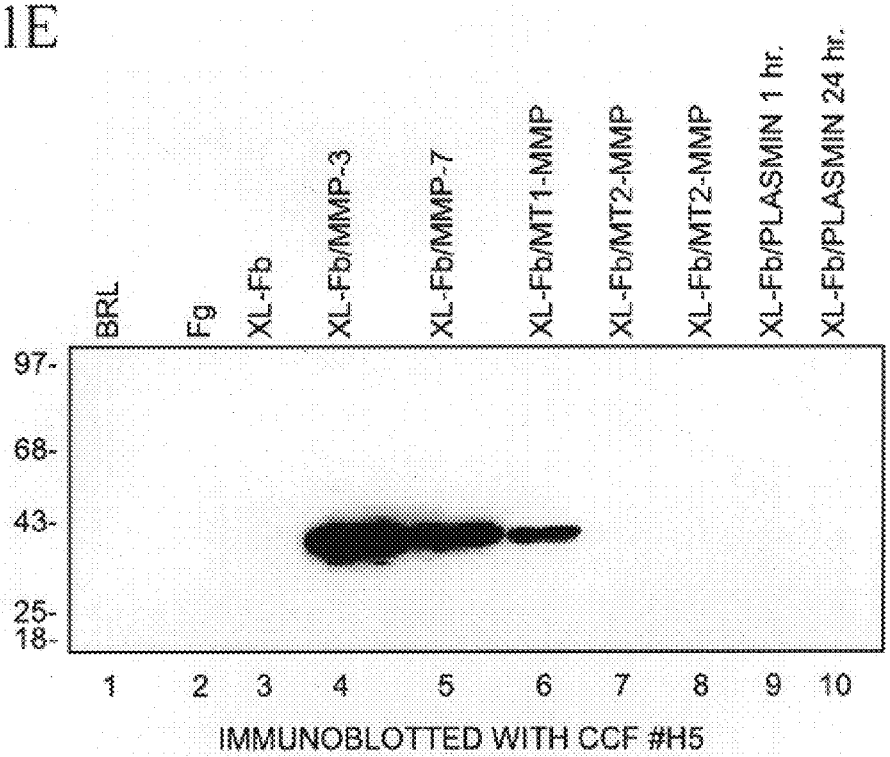
FIGS. 1E and 1F, Two new antibodies, Clone Culture Fluid (CCF)#H5 and #F2 were used on electroblotted purified preparations of cross-linked fibrin digested with MMP-3, -7, MT1-MMP, MT-2 MMP and plasmin (same samples and order in FIGS. 1E and 1F).
Figure 1F:
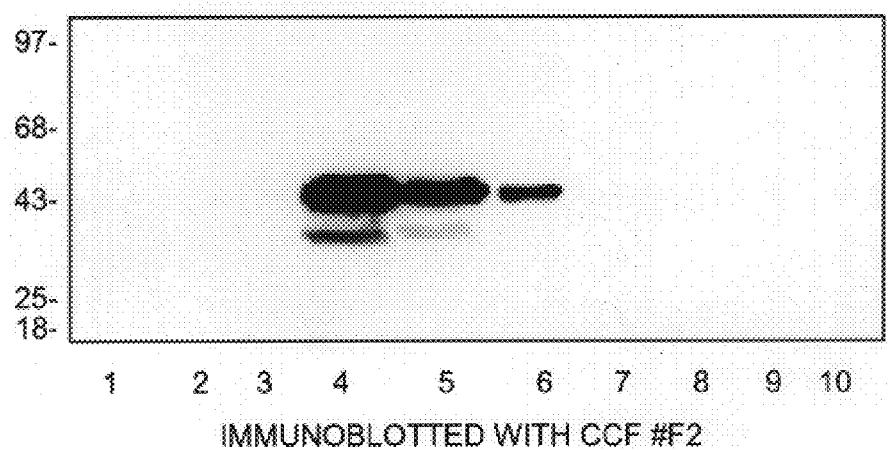

As shown in FIGS. 1A and 1B, clone culture fluid #29 and monoclonal antibody H5 reacted with a fibrin(ogen)-derived fragment present in human synovial fluid with the same molecular mass of fragments derived after degradation of XL-Fb with MMP-3 (FIG. 1B), MMP-7 and MT1-MMP (FIG. 1E) in purified system. Clone Culture Fluid (CCF)#29 is a parent line from which MoAb F2 was subcloned. Also, further purification of fibrin(ogen)-derived protein from synovial fluid was done by affinity chromatography on MoAb/2N3H10, an anti-Fibrin(ogen) fragment E antibody that was previously developed in our laboratory. D/D dimers are not bound by the 2N3H10 column, whereas intact fibrin(ogen) and fragment E are bound and retained. A fragment in a flow-through fraction of the column that did not bind to MoAb/2N3H10 reacted with both MoAb/H5 and F2 (FIGS. 1C and 1D).

Figure 1G:
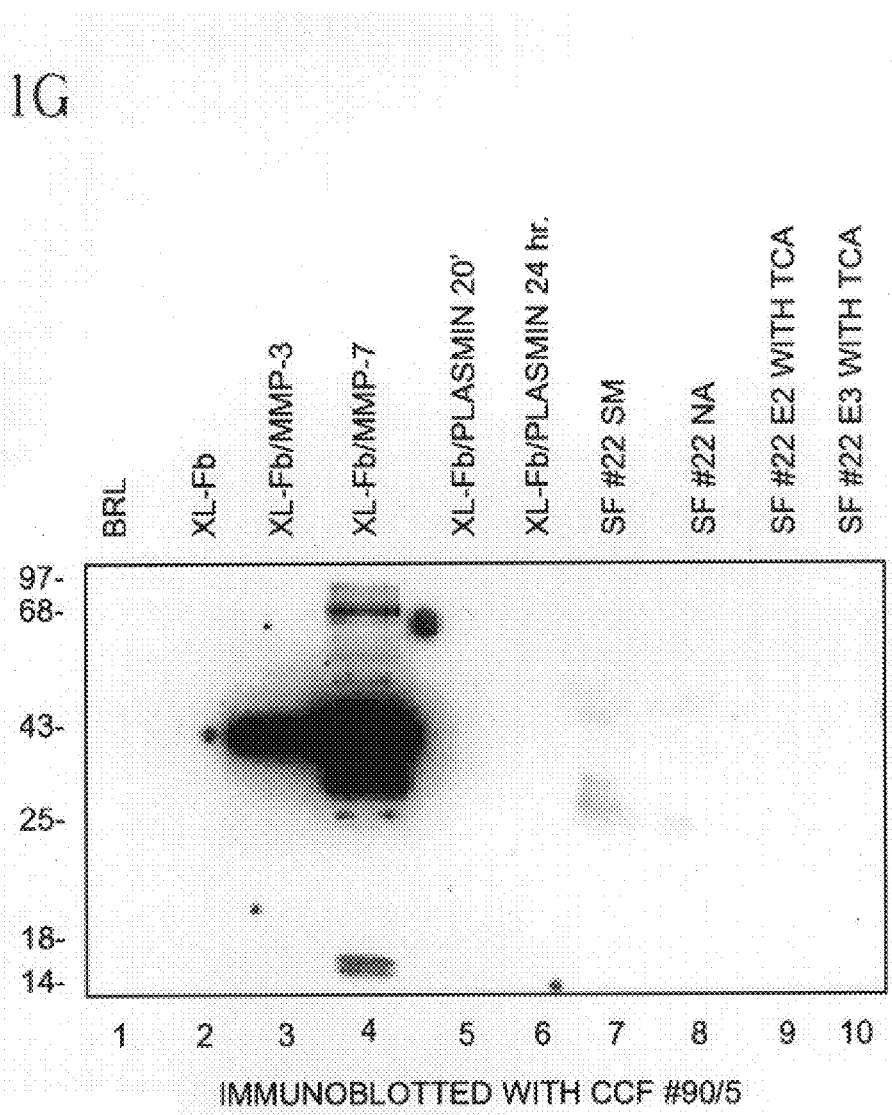
Figure 2:
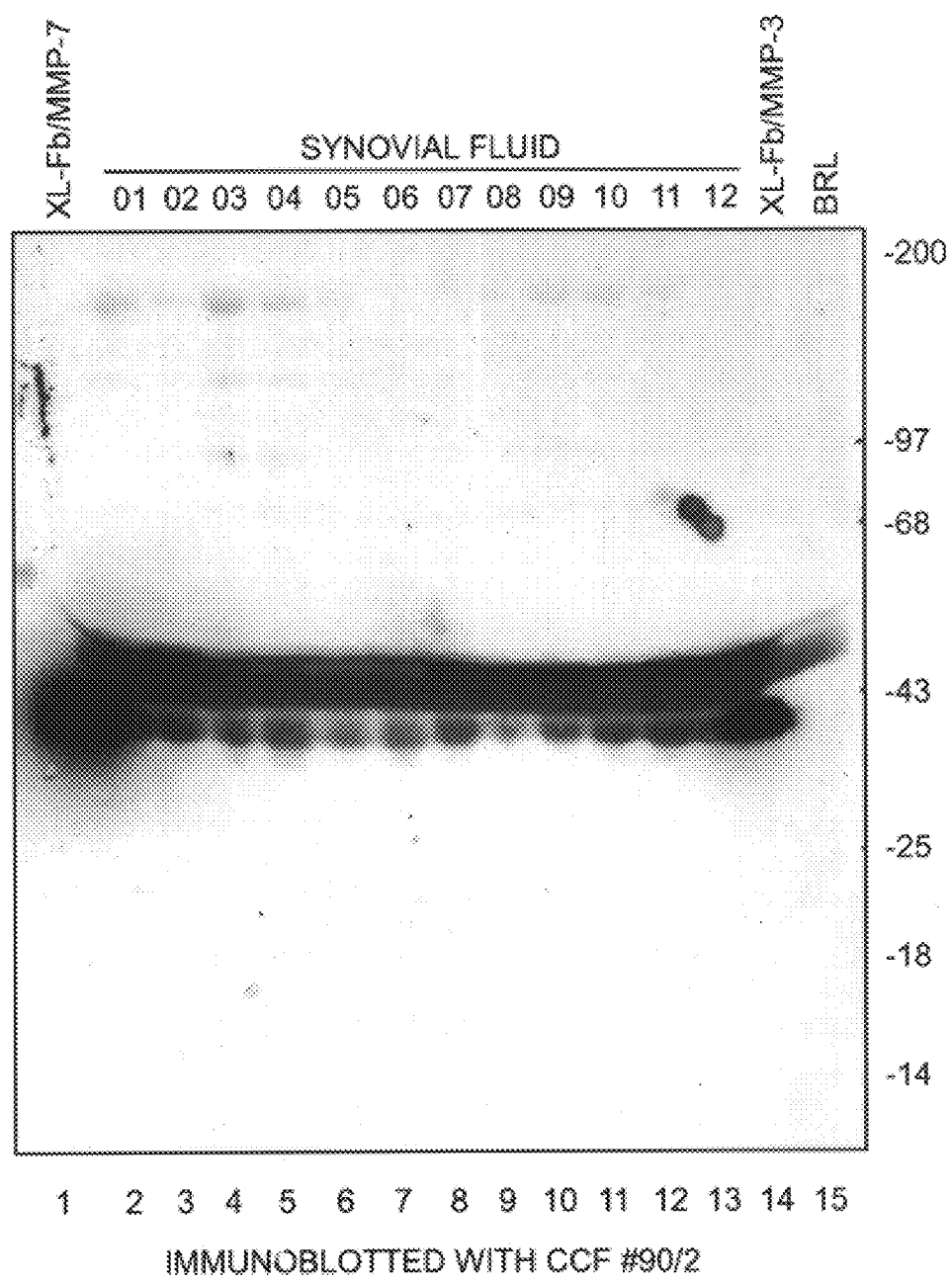
FIG. 2 illustrates the detection of MMP-3, -7/degraded fibrin(ogen) in human synovial fluids. A new antibody, CCF#90/2 was used on electroblotted purified preparations of XL-Fb digested with MMP-3 and -7 (lanes 1, 12). Synovial fluid samples from patients with rheumatoid arthritis, osteoarthritis and other inflammatory and non-inflammatory arthritides were electroblotted with CCF#90/2 (lanes 2–13).

Four subclones were selected from the fusion obtained after immunization of the animals with XL-Fb fully digested with MMP-7, namely 90/2, 90/5, 197/1, and 197/2. As shown in FIG. 1G, MoAb 90/5 reacts with XL-Fb fully digested with MMP-3 and -7 gamma chains (lanes 3, 4) but not with XL-Fb or early and late digest of XL-Fb with plasmin (FIG. 1G, lanes 2, 5, 6). That antibody also reacts with a fibrin(ogen) fragment present in the intact and non-adsorbed fraction of synovial fluid from a patient with rheumatoid arthritis (FIG. 1G, lanes 7, 8). Similarly, another antibody, MoAb 90/2 reacts with a fragment present in synovial fluid from patients with rheumatoid arthritis, osteoarthritis and other arthritides (FIG. 2, lanes 2–13), that is also present in XL-Fb digested with MMP-3 and -7 (FIG. 2, lanes 1, 14). MoAbs 197/1 and 197/2 also react with cross-linked fibrin digested with MMP-3 and MMP-7 and do not react with cross-linked fibrin and plasmin-digested cross-linked fibrin.

Since intact Fg, XL-Fb and early and late plasmin digest of XL-Fb fail to react with these antibodies, patient plasma, body fluids and tissues reactive with antibodies H5, F2, 90/2, 90/5 and others derived from those two fusions are indicative of in vivo degradation of fibrin(ogen) by MMP-3, -7 and MT1-MMP. These antibodies are the first antibodies that have ever been described to be specific for epitopes present in digests of fibrin(ogen) degraded with MMP-3 and MMP-7. The lysis of fibrin(ogen) and cross-linked fibrin by MMPs may be relevant in many, if not all of these pathophysiological processes.

Example 3

Assays (RIA, ELISA, immunoblot analysis) using MoAbs H5, F2, 90/2, 90/5 and others derived from the same fusions, are useful in detecting in vivo proteolysis of fibrin (ogen) by MMP-3, 7, MT1-MMP or other, yet to be tested MMPs. Since Fg, XL-Fb and early and late digest of XL-Fb with plasmin are totally unreactive with antibodies H5, F2, 90/2 and 90/5 (and possibly others MoAbs derived from the same fuisions), any reactivity with plasma, other body fluids and tissue fibrin(ogen)-derived deposits would be strongly suggestive of in vivo presence of MMP-3, -7 and MT1-MMP activity on fibrin(ogen). As shown in FIGS. 1A–1D and 1G, D-and D-dimer fragment-derived beta chains (a–d) and gamma chains of fibrin(ogen) were detected in synovial fluids with the above described antibodies.

These data provide evidence of the existence and detectability of MMPs-derived fibrin(ogen) fragments in vivo by our antibodies. Those antibodies are useful in early detection and diagnosis of inflammatory and non-inflammatory joint disease such as rheumatoid arthritis, osteoarthritis and other in which fibrin deposits are present in the affected joints and degraded by a number of proteases including plasmin and possibly MMPs. Moreover, those antibodies could be utilized to evaluate the proteolytic activity of MMPs in angiogenesis and a number of diseases in which circulating or tissue FDPs were previously detected such as inflammation, atherosclerosis, renal disease, malignancy and others. Moreover, these antibodies may be utilized to study fibrin formation and degradation in physiological processes such as in wound healing and in the development of human placenta and placenta development diseases.

More recently the inventors have also shown that MMP-7 (or Matrilysin) (Bini et al. *Blood* 90 (10):Suppl 1 465a, 1997) and MT1-MMP (Bini et al, *Biochemistry* 1999 October 19;38(42):13928–36) also have the ability to solubilize XL-Fb clots. However, their mechanisms of action appear different from MMP-3. MMP-7 and MT1-MMP each generate a fragment D-dimer from degradation of XL-Fb, similarly in size that generated by plasmin, but with different amino-termini.

In these studies the present inventors have shown by aminio-terminal sequence analysis that the cleavage sites for MPM-3, -7 and MT1-MMP are different from those cleaved by plasmin. Also, recently it has been shown that MMP-3 codistributes with fibrin deposits in atherosclerotic plaques (Bini et al., *Arterioscler Thromb Vasc Biol* 1999 August; 19(8):1852–61).

Example 4

In addition to the previous MoAbs (H5, F2, 90/2 and 90/5) five additional subclones have been isolated and partially characterized, namely B4, I3, C6, 197/1, 197/2 (and others still not fully characterized, including A6, G6 and E6) from previous fusion experiments (using spleen cells of animals sensitized with XL-Fb fully digested with MMP-3 or MMP-7). In using mixtures of such degradation products as immunogen, we have identified antibodies specific for fibrin (ogen) degradation products (FDPs) generated with MMP-3 and -7, but not reactive with intact Fg, XL-Fb or early and late FDPs generated by degradation of fibrin(ogen) with plasmin.

Partial characterization has determined that antibodies F2, H5, B4, I3 and C6 react with the beta chain of the D/D-dimer ($\beta$121-461) generated in fibrin(ogen) digests made with MMP-3 and MMP-7. Antibodies 90/2, 90/5, 197/1 and 197/2 react with an epitope present in either the beta ($\beta$121-461) or gamma chain ($\gamma$84-404) of the D/D-dimer fragments generated after degradation of fibrin(ogen) with MMP-3 and MMP-7.

These antibodies are the first antibodies that have ever been described to be specific for epitopes present in digests of fibrin(ogen) degraded with MMP-3 and MMP-7.

The mouse lymphocyte hybridomas H5 and 90/2 described herein were deposited with the American Type Culture Collection (ATCC), Manassas, Va. 20110-2209, on Jan. 31, 2002 under the terms of the Budapest Treaty and assigned Patent Deposit Designations of PTA-4023 and PTA-4024, respectively.

EQUIVALENTS

Those of skill in the art will immediately recognize the utility and scope of the antibodies, assays and methods of the present invention as compositions and in the detection, diagnosis, monitoring and identification of Fibrin(ogen) digestion products generated by matrix metalloproteinases. The disclosures of the U.S. Patents cited herein are useful in the practice of the full scope of the invention. The full texts of these U.S. patents are hereby incorporated by reference.

What is claimed is:

1. A hybridoma cell line H5 deposited with American Type Culture Collection (ATCC) as accession number PTA-4023.

2. A hybridoma cell line 90/2 deposited with American Type Culture Collection (ATCC) as accession number PTA-4024.

3. An isolated monospecific antibody which specifically binds a fibrin(ogen) degradation product (FDP) generated by matrix metalloproteinase (MMP)-3 and/or MMP-7 digestion and does not specifically bind any fibrin(ogen) degradation product generated by plasmin enzymatic activity said monospecific antibody selected from a monoclonal antibody having all identifying characteristics of antibody H5 produced by the hybridoma cell line of claim 1 or having all identifying characteristics of antibody 90/2 produced by the hybridoma cell line of claim 2, a FDP-binding fragment of said monoclonal antibody or a FDP-binding chimeric antibody comprising either of said fragment or all complementarity determining variable region amino acid sequences of said monoclonal antibody.

4. The monospecific antibody according to claim 3, wherein the monospecific antibody is labeled with a detectable moiety.

5. The monospecific antibody according to claim 4, wherein the detectable moiety is selected from the group consisting of a radioactive label, an enzyme, a specific binding pair component, a colloidal dye substance, a fluorchrome, a reducing substance, a latex, digoxigenin, a metal, a particulate, dansyl lysine, an antibody, protein A, protein G, protein L, an electron dense material, and a chromophore.

6. The monospecific antibody according to claim 3, wherein the monospecific antibody is attached to a solid or substantially solid substrate.

7. The monospecific antibody according to claim 6, wherein the solid or substantially solid substrate includes a component selected from the group consisting of a gel, a hydrogel, a resin, a bead, nitrocellulose, a nylon filter, a microtiter plate, a culture flask, and a polymeric material.

8. The monospecific antibody according to claim 3, wherein the monospecific antibody is the monoclonal antibody H5 produced by the hybridoma cell line H5 of claim 1.

9. The monospecific antibody according to claim 3, wherein the monospecific antibody is the monoclonal antibody 90/2 produced by the hybridoma cell line 90/2 of claim 2.

10. A method of detecting a fibrin(ogen) degradation product (FDP) generated by matrix metalloproteinase (MMP)-3 and/or MMP-7 in a sample, the method comprising: contacting the sample with the monospecific antibody of claim 3, and detecting presence or level of specific binding of the monospecific antibody with FDP in the sample.

11. The method according to claim 10, wherein the sample is a biological sample.

12. The method according to claim 11, wherein sample is tested in vitro.

13. The method according to claim 10, wherein the method is an immunochemical method.

14. The method according to claim 13, wherein said immunochemical method is selected from the group consisting of an enzyme-linked immunosorbent assay (ELISA), immunonephelometry, agglutination, precipitation, immunodiffision, immuno-electrophoresis, immunofluorescence, and a radioimmunoassay.

15. The method according to claim 10, wherein the monospecific antibody is labeled with a detectable moiety.

16. The method according to claim 15, wherein the detectable moiety is selected from the group consisting of a radioactive label, an enzyme, a specific binding pair component, a colloidal dye substance, a fluorophore, a reducing substance, a latex, digoxigenin, a metal, a particulate, dansyl lysine, an antibody, protein A, protein G, protein L, an electron dense material, and a chromophore.

17. The method according to claim 10, wherein the monospecific antibody is attached to a solid or substantially solid substrate.

18. The method according to claim 17, wherein the solid substrate includes a component selected from the group consisting of a gel, a hydrogel, a resin, a bead, nitrocellulose, a nylon filter, a microtiter plate, a culture flask, and a polymeric material.

19. The method according to claim 10, wherein the monospecific antibody is the monoclonal antibody H5 produced by the hybridoma cell line H5 of claim 1.

20. The method according to claim 10, wherein the monospecific antibody is the monoclonal antibody 90/2 produced by the hybridoma cell line 90/2 of claim 2.

21. A kit for the detection of a fibrin(ogen) digestion product (FDP) generated by matrix metalloproteinase MMP)-3 and/or MMP-7, comprising:
   a) a composition comprising the monospecific antibody of claim 3, and
   b) a component selected from the group consisting of: a suitable buffer, an FDP standard and a component for detection of the monospecific antibody.

22. The kit according to claim 21, wherein the monospecific antibody is labeled with a detectable moiety.

23. The kit according to claim 21, wherein the monospecific antibody is attached to a solid substrate.

24. The kit according to claim 21, wherein the monospecific antibody is the monoclonal antibody H5 produced by the hybridoma cell line H5 of claim 1.

25. The kit according to claim 21, wherein the monospecific antibody is the monoclonal antibody 90/2 produced by the hybridoma cell line 90/2 of claim 2.

* * * * *

UNITED STATES PATENT AND TRADEMARK OFFICE
CERTIFICATE OF CORRECTION

PATENT NO.    : 6,451,599 B1
DATED         : September 17, 2002
INVENTOR(S)   : Bini et al.

It is certified that error appears in the above-identified patent and that said Letters Patent is hereby corrected as shown below:

<u>Title page,</u>
Item [57], ABSTRACT,
Line 2, now reads "degradation products (FDPS)" should read -- degradation products (FDPs) --
Line 7, now reads "B4, 13" should read -- B4, I3 --

<u>Column 1,</u>
Line 13, now reads "fibrin(ogen) egradation", should read -- fibrin(ogen) degradation --

<u>Column 2,</u>
Line 58, now reads "Factor X11Ia", should read -- Factor XIIIa --

<u>Column 5,</u>
Line 38, now reads "13", should read -- I3 --

<u>Column 6,</u>
Line 24, now reads "13", should read -- I3 --

<u>Column 15</u>
Line 14, now reads "express fuision", should read -- express fusion --

Signed and Sealed this

Eighth Day of April, 2003

JAMES E. ROGAN
*Director of the United States Patent and Trademark Office*